(12) United States Patent
Bern

(10) Patent No.: US 11,457,322 B2
(45) Date of Patent: Sep. 27, 2022

(54) IMPLANTABLE DUAL-VIBRATOR HEARING SYSTEM

(71) Applicant: Oticon Medical A/S, Smørum (DK)

(72) Inventor: Bengt Bern, Mölndal (SE)

(73) Assignee: OTICON MEDICAL A/S, Smørum (DK)

(*) Notice: Subject to any disclaimer, the term of this patent is extended or adjusted under 35 U.S.C. 154(b) by 716 days.

(21) Appl. No.: 16/405,731

(22) Filed: May 7, 2019

(65) Prior Publication Data

US 2019/0349695 A1 Nov. 14, 2019

(30) Foreign Application Priority Data

May 8, 2018 (EP) .................................... 18171194

(51) Int. Cl.
*H04R 25/00* (2006.01)
*A61N 1/372* (2006.01)

(52) U.S. Cl.
CPC ......... *H04R 25/65* (2013.01); *A61N 1/37223* (2013.01); *H04R 2225/67* (2013.01)

(58) Field of Classification Search
CPC .... H04R 25/65; H04R 25/554; H04R 25/606; H04R 2225/67; H04R 1/24; H04R 2460/03; H04R 25/604; H04R 2460/13; A61N 1/37223; A61F 2250/0001; A61F 2250/00

See application file for complete search history.

(56) References Cited

U.S. PATENT DOCUMENTS

| 5,879,283 A * | 3/1999 | Adams ................. H04R 25/606 600/25 |
| 2007/0191673 A1 | 8/2007 | Ball et al. |
| 2010/0190436 A1 | 7/2010 | Cook et al. |
| 2012/0022613 A1* | 1/2012 | Meskens ................ H02J 7/025 607/57 |

(Continued)

FOREIGN PATENT DOCUMENTS

| EP | 3 306 955 A1 | 4/2018 |
| WO | WO-2017120357 A1 * | 7/2017 .............. H02J 50/12 |
| WO | WO 2018/051646 A1 | 3/2018 |

OTHER PUBLICATIONS

Samsita, "Advantages and Disadvantages of Amplitude Modulation" Nov. 30, 2015, Electronics Post. (Year: 2015).*

*Primary Examiner* — Christine H Matthews
*Assistant Examiner* — Joshua Daryl D Lannu
(74) *Attorney, Agent, or Firm* — Birch, Stewart, Kolasch & Birch, LLP

(57) ABSTRACT

An implantable unit of a transcutaneous hearing device and a transcutaneous hearing device comprising the same is disclosed. The implantable unit comprises a receiver element configured to wirelessly receive an electromagnetic wave, a rectifier element configured to generate upper and lower half waveforms of the electromagnetic wave, and a vibrator element configured to electromechanically produce vibration using the half waveforms of the electromagnetic wave. The vibrator element comprises a first vibrator and a second vibrator. The first vibrator is configured to be driven by the upper half waveform of the electromagnetic wave, and the second vibrator is configured to be driven by the lower half waveform of the electromagnetic wave.

12 Claims, 7 Drawing Sheets

(56) References Cited

U.S. PATENT DOCUMENTS

| | | | |
|---|---|---|---|
| 2015/0208183 A1* | 7/2015 | Bern | H04R 25/65 |
| | | | 381/326 |
| 2015/0281854 A1* | 10/2015 | Nikles | H04R 25/30 |
| | | | 381/323 |
| 2017/0180887 A1* | 6/2017 | Meskens | H02J 7/025 |
| 2018/0077504 A1 | 3/2018 | Shaquer et al. | |
| 2019/0052981 A1 | 2/2019 | Kuno | |

* cited by examiner

IMPLANTABLE DUAL-VIBRATOR HEARING SYSTEM

FIELD

The present disclosure relates to an implantable dual-vibrator hearing system. More particularly, the present disclosure relates to an implantable unit of a transcutaneous hearing device and a transcutaneous hearing device comprising the same.

BACKGROUND

In bone-conductive hearing aids, there is a trend of transitioning from a percutaneous system to a transcutaneous system in which a wireless link is used to transfer an electromagnetic wave (carrying energy and signal) from an external unit (operable as audio processor) placed on/above the skin to an implanted/implantable unit placed under the skin. However, when transitioning from a percutaneous hearing device to a transcutaneous hearing device, there is a loss of energy in the wireless link of typically around 10 dB. This means that a transcutaneous hearing device where a vibrator element is implantable (i.e. implemented in the implanted/implantable unit) will always be weaker than a percutaneous hearing device where a vibrator element is not implantable.

Accordingly, there is a problem in that the vibrator element (in the implanted unit) of a transcutaneous (bone-conductive) hearing device can only be driven with reduced energy, as compared with a percutaneous (bone-conductive) hearing device.

Therefore, there is a need to provide a solution that addresses such problem of loss of energy over the wireless link of a transcutaneous (bone-conductive) hearing device, i.e. loss of driving energy for the vibrator element.

SUMMARY

Various embodiments of the present disclosure aim at addressing at least part of the above issues and/or problems and drawbacks.

Various aspects of embodiments of the present disclosure are set out in the appended claims.

According to a first aspect of the present disclosure, there is provided an implantable unit of a transcutaneous hearing device. The implantable unit comprises a receiver element configured to wirelessly receive an electromagnetic wave, a rectifier element configured to generate upper and lower half waveforms of the electromagnetic wave, and a vibrator element configured to produce vibration using the half waveforms of the electromagnetic wave. The vibrator element is configured to electromechanically or piezo-electric produce vibration. The vibrator element comprises a first vibrator configured to be driven by the upper half waveform of the electromagnetic wave and a second vibrator configured to be driven by the lower half waveform of the electromagnetic wave.

According to another aspect of the present disclosure, there is provided an implantable device configured to be used in a transcutaneous hearing device, comprising a receiver element configured to wirelessly receive an electromagnetic wave, a rectifier element configured to generate upper and lower half waveforms of the electromagnetic wave, and a vibrator element configured to electromechanically produce vibration using the half waveforms of the electromagnetic wave, wherein the vibrator element comprises a first vibrator configured to be driven by the upper half waveform of the electromagnetic wave and a second vibrator configured to be driven by the lower half waveform of the electromagnetic wave.

The implantable device is similar to the implantable unit.

The first vibrator may be a vibrator including a coil and a permanent magnet, or, the first vibrator may be a piezo-electric vibrator.

The second vibrator may be a vibrator including a coil and a permanent magnet, or, the second vibrator may be a piezo-electric vibrator.

The first vibrator is connected to the rectifier element and is configured to receive the upper half waveform or the lower half waveform of the electromagnetic wave, and thereby be driven by either the upper half waveform or the lower half waveform.

The second vibrator is connected to the rectifier element and is configured to receive the upper half waveform or the lower half waveform of the electromagnetic wave, and thereby be driven by either the upper half waveform or the lower half waveform.

The rectifier element may include a first diode and a second diode connected to the first vibrator and the second vibrator, respectively, or vice versa.

With such configuration, the vibrator element can be driven with increased energy, as compared with a conventional transcutaneous (bone-conductive) hearing device. Stated in other words, the loss of energy over the wireless link can at least partly be compensated or reduced.

According to various implementations and/or developments of the first aspect, one or more of the following applies.

The rectifier element may comprise a first diode in a path from the receiver element to the first vibrator of the vibrator element.

The rectifier element may comprise a second diode in a path from the receiver element to the second vibrator of the vibrator element.

The first diode and the second diode may be connected with mutually opposite polarity between the receiver element and the vibrator element.

One of the first and second vibrators may be a high-frequency vibrator configured to produce high-frequency vibration.

The other of the first and second vibrators may be a low-frequency vibrator configured to produce low-frequency vibration.

The receiver element may be configured to receive an amplitude-modulated electromagnetic wave.

The rectifier element may be configured to demodulate an amplitude-modulated electromagnetic wave and to generate upper and lower half waveforms of the amplitude-demodulated electromagnetic wave.

The receiver element may comprise an induction component, such as a coil, configured to inductively receive the electromagnetic wave.

The vibrator element may be constituted by one component part or module comprising the first vibrator and the second vibrator.

The vibrator element may be constituted by two component parts or modules, each of which comprising one of the first vibrator and the second vibrator.

The implantable unit may be configured to be fixed to a skull of a user of the transcutaneous hearing device.

The receiver element may be configured to be placed in a border area of the temporal bone and the parietal bone of a skull of a user of the transcutaneous hearing device.

The first and second vibrators may be configured to be placed at basically the same position of a skull of a user of the transcutaneous hearing device, or the one of the first and second vibrators being a high-frequency vibrator is configured to be placed at the skull to be closer to the cochlea than the other of the first and second vibrators being a low-frequency vibrator.

The implantable unit may be operable as a variable reluctance transducer of a Bonebridge system, a Bone Conduction Implant system, or a Balanced Electromagnetic Separation Transducer system.

According to a second aspect of the present disclosure, there is provided a transcutaneous hearing device. The transcutaneous hearing device comprises an implantable unit according to the aforementioned first aspect, and an external unit configured to operate as an audio processor.

According to various implementations and/or developments of the second aspect, one or more of the following applies.

The external unit may comprise a detector element configured to detect sound.

The external unit may comprise a processing element configured to generate a sound signal based on detected sound.

The external unit may comprise a transmitter element configured to wirelessly transmit an electromagnetic wave based on a sound signal.

BRIEF DESCRIPTION OF THE DRAWINGS

In the following, the present disclosure will be described in greater detail by way of non-limiting examples with reference to the accompanying drawings. Aspects, features and/or technical effects of the present disclosure will be apparent from and elucidated with reference to the drawings described hereinafter in which.

DETAILED DESCRIPTION

Figure 1:
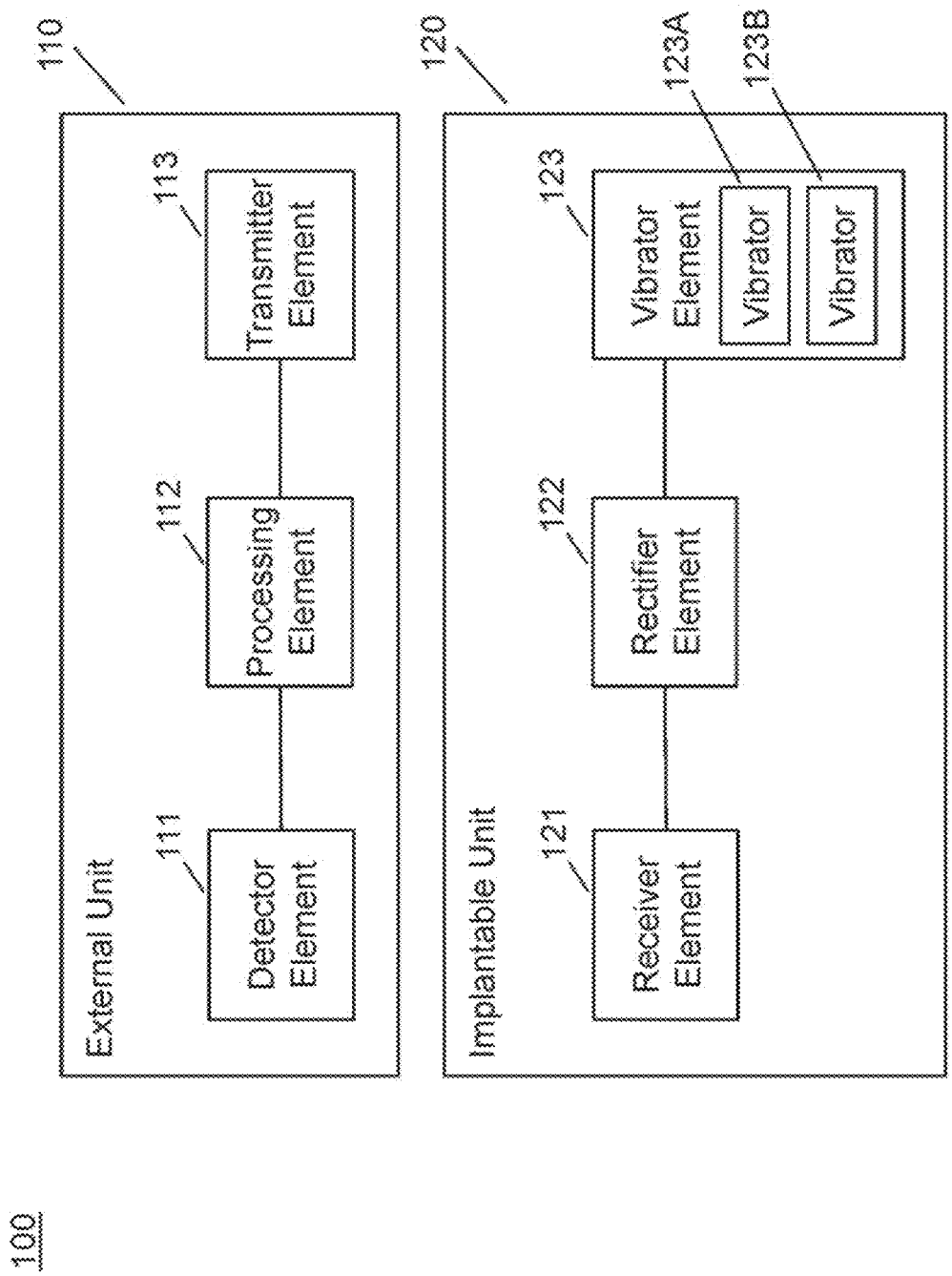
FIG. 1 illustrates a schematic block diagram of a transcutaneous hearing device according to an embodiment of the present disclosure.

The present disclosure is described herein with reference to particular non-limiting examples and to what are presently considered to be conceivable embodiments. A person skilled in the art will appreciate that the present disclosure is by no means limited to these examples and embodiments, and may be more broadly applied.

The detailed description set forth below in connection with the accompanying drawings is intended as a description of various configurations. Yet, any other system configuration or deployment may equally be utilized as long as complying with what is described herein and/or example embodiments described herein are applicable to it.

The detailed description includes specific details for the purpose of providing a thorough understanding of various concepts. However, it will be apparent to those skilled in the art that these concepts may be practiced without these specific details. It is generally to be noted that, according to certain needs and constraints, all of the described variants and/or alternatives may be provided alone or in any conceivable combination (also including combinations of individual features of the various variants and/or alternatives). In this description, the words "comprising" and "including" should be understood as not limiting the described example embodiments and implementations to consist of only those features that have been mentioned, and such example embodiments and implementations may also contain features, structures, units, modules etc. that have not been specifically mentioned.

Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout the present disclosure. A computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

In the drawings, it is to be noted that lines/arrows interconnecting individual blocks or entities are generally meant to illustrate an operational coupling there-between, which may be a physical and/or logical coupling, which on the one hand is implementation-independent (e.g. wired or wireless) and on the other hand may also comprise an arbitrary number of intermediary functional blocks or entities not shown.

According to example embodiments of the present disclosure, in general terms, there is provided an implantable dual-vibrator hearing system. More particularly, the present disclosure provides an implantable unit of a transcutaneous hearing device and a transcutaneous hearing device comprising the same.

FIG. 1 illustrates a schematic block diagram of a transcutaneous hearing device according to an embodiment of the present disclosure. The thus illustrated transcutaneous hearing device may be implemented as a transcutaneous hearing device or system of bone-conductive type.

As illustrated in FIG. 1, a transcutaneous hearing device 100 according to an embodiment comprises an external unit 110 and an implantable (or implanted) 120.

The external unit 110 is preferably configured to operate as an audio processor. The external unit 110 may comprises a detector element 111 which is configured to detect sound, a processing element 112 which is configured to generate a sound signal based on the detected sound, and a transmitter element 113 which is configured to wirelessly transmit a electromagnetic wave based on the sound signal.

The implantable (or implanted) unit 120 is preferably configured to operate as a bone vibration unit for transferring sound to the skull of user of the hearing device. The implantable (or implanted) unit 120 comprises a receiver element 121 which is configured to wirelessly receive an electromagnetic wave (which is transmitted from the transmitter element 113 of the external unit 110), a rectifier element 122 which is configured to generate upper and lower half waveforms of the electromagnetic wave, and a vibrator element 123 which is configured to electromechanically produce vibration using the half waveforms of the electromagnetic wave. The vibrator element 123 comprises at least two vibrators being driven by the half waveforms of the electromagnetic wave (which are generated by the rectifier element 122). As illustrated in FIG. 1, the vibrator element 123 preferably comprises a first vibrator 123A which is configured to be driven by the upper half waveform of the electromagnetic wave and a second vibrator 123B configured to be driven by the lower half waveform of the electromagnetic wave.

According to an embodiment, the one of the first and second vibrators may be a high-frequency vibrator which is configured to produce high-frequency vibration, and the other of the first and second vibrators may be a low-frequency vibrator which is configured to produce low-frequency vibration. For example, low-frequency vibration may have a frequency range starting from 124 Hz (as the lower limit), and high-frequency vibration may have a frequency range starting from 8 kHz or 2 kHz (as the lower limit).

According to an embodiment, the vibrator element 123 may be constituted by one component part or module comprising the first vibrator 123A and the second vibrator 123. According to another embodiment, the vibrator element 123 may be constituted by two component parts or modules, each of which comprising one of the first vibrator 123A and the second vibrator 123B.

Generally, the implantable unit 120 is configured to be implantable (so as to become an implanted unit when being installed and operative). That is, the implantable unit 120 is configured to fixed to a skull of a user of the transcutaneous hearing device. An example of a possible placement thereof is describe below with reference to FIG. 7.

Also, the implantable unit 120 may be operable as a transducer of any kind of (bone-conductive) hearing device or system, including (but not limited to) a Bonebridge system such as a Medel Bonebridge, a Bone Conduction Implant (BCI) system, or a Balanced Electromagnetic Separation Transducer (BEST) system, for example.

Figure 2:
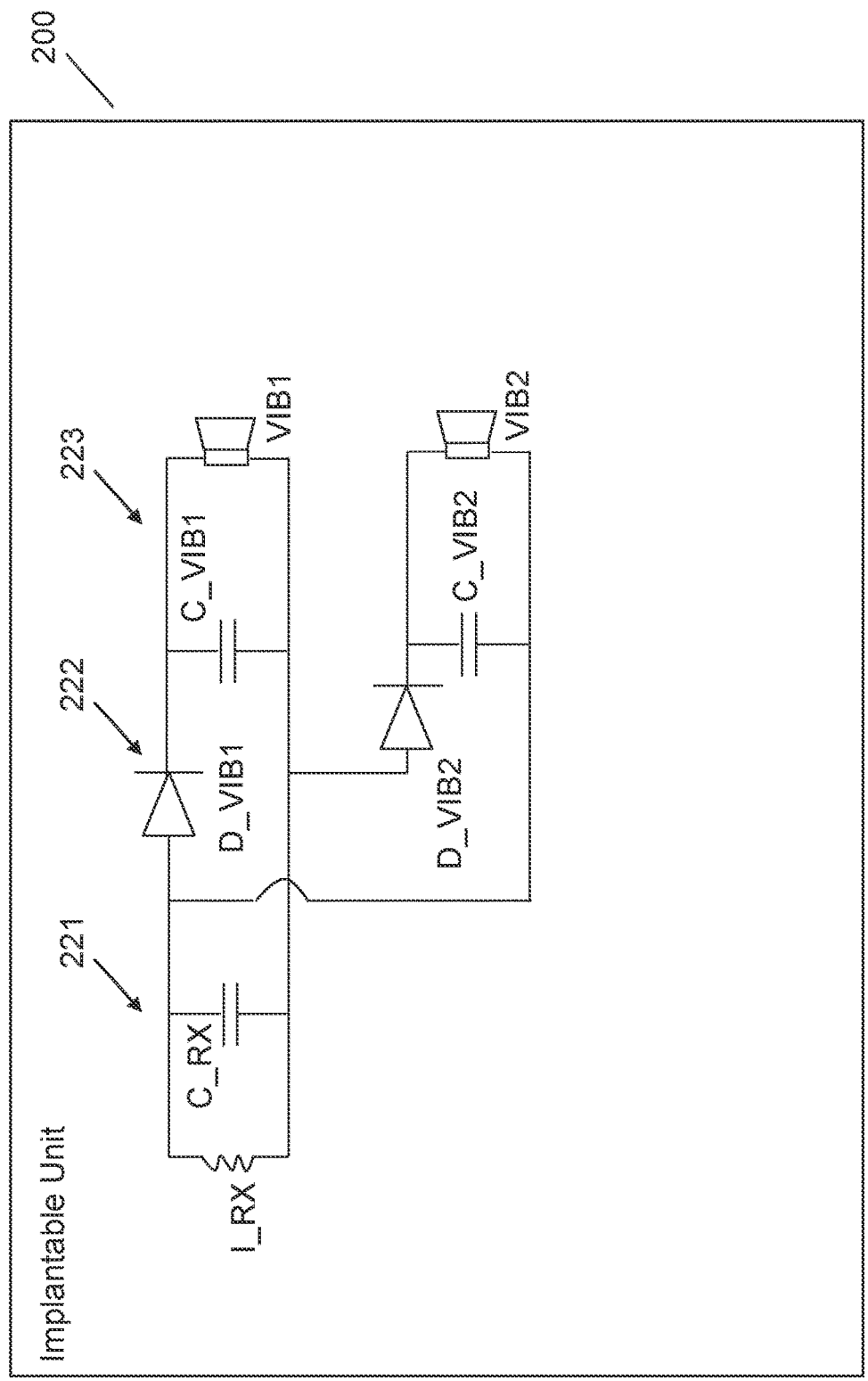
FIG. 2 illustrates a schematic circuit diagram of an example of an implantable unit according to an embodiment of the present disclosure.

FIG. 2 illustrates a schematic circuit diagram of an example of an implantable unit according to an embodiment of the present disclosure. The thus illustrated implantable unit may be implemented, as implantable (or implanted) unit 110 in the transcutaneous hearing device 100 as illustrated in FIG. 1.

As illustrated in FIG. 2, an implantable unit 200 according to an embodiment comprises a receiver element 221, a rectifier element and a vibrator element 223.

The receiver element 221 may preferably be configured to receive an amplitude-modulated electromagnetic wave. In the illustrated example implementation, the receiver element 221 comprises an induction component I_RX, such as a coil, which is configured to inductively receive the electromagnetic wave, and may further comprise a capacitance component C_RX, such as a capacitor, in parallel connection with the induction component I_RX.

The rectifier element 222 may preferably be configured to demodulate the amplitude-modulated electromagnetic wave and to generate upper and lower half waveforms of the amplitude-demodulated electromagnetic wave.

The rectifier element 222 may also be configured to apply a smoothing operation on the amplitude-modulated electromagnetic wave. In the illustrated example implementation, the rectifier element 222 comprises a first diode D_VIB1 in a path from the receiver element 221 to the first vibrator VIB1 of the vibrator element 223 and a second diode D_VIB2 in a path from the receiver element 221 to the second vibrator VIB2 of the vibrator element 223. In the illustrated example implementation, the first diode D_VIB1 and the second diode D_VIB2 are connected with mutually opposite polarity, i.e. in anti-parallel manner or relation, between the receiver element 221 and the vibrator element 223.

The vibrator element 223 may preferably be configured to produce vibration, which is exerted to the skull of a user of the hearing device when being installed and operative. In the illustrated example implementation, the vibrator element 223 comprises a first vibrator VIB1 and a second vibrator VIB2, and may further comprise capacitance components C_VIB1 and C_VIB2, such as capacitors, in parallel connection with the vibrators VIB1 and VIB2, respectively. For example, the first vibrator VIB1 may be a low-frequency (LF) vibrator to produce low-frequency (LF) vibration, and the second vibrator VIB2 may be a high-frequency (HF) vibrator to produce high-frequency (HF) vibration, or vice versa.

Figure 3:
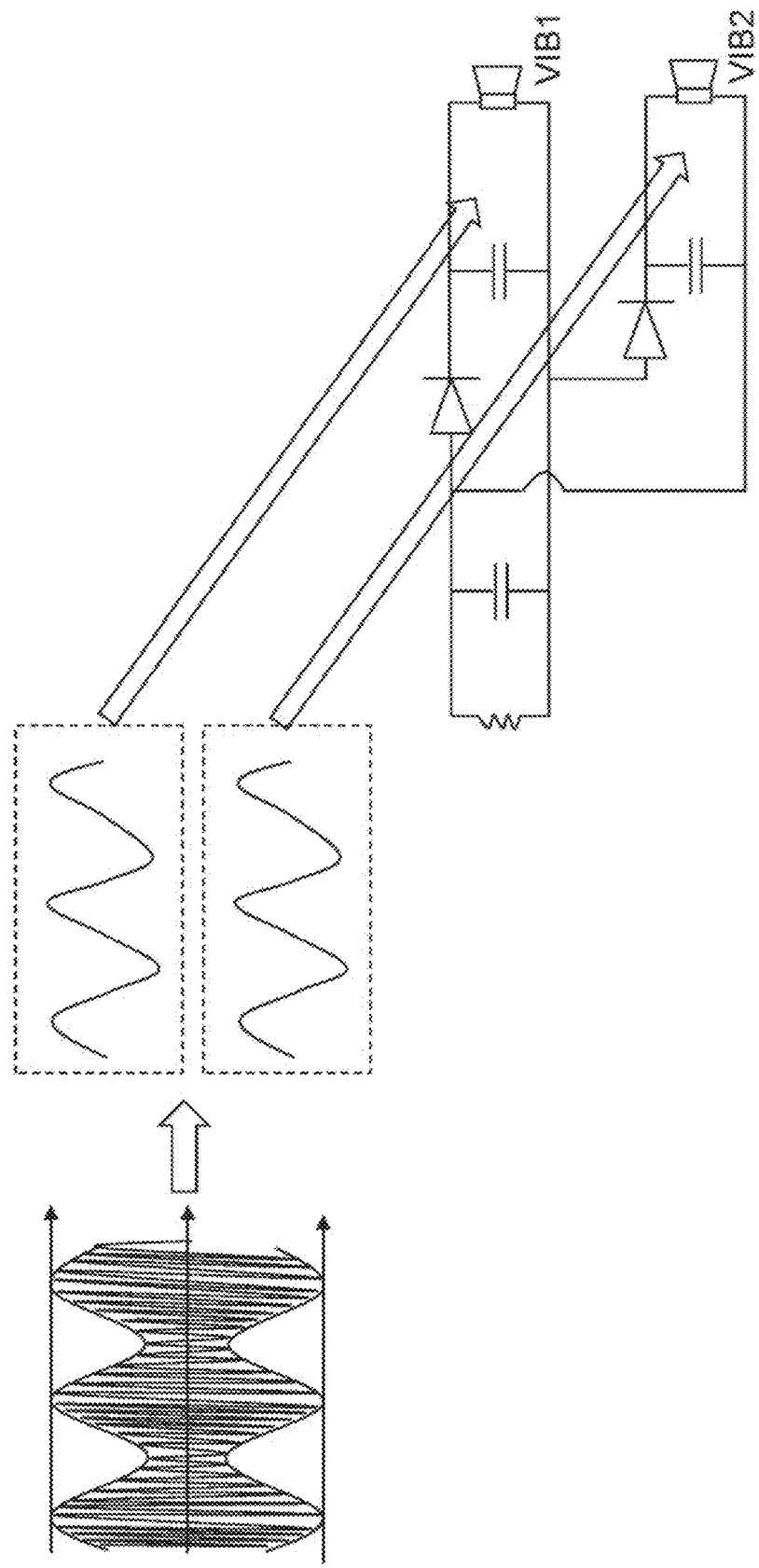
FIG. 3 illustrates a schematic diagram of the operational concept of a transcutaneous hearing device according to an embodiment of the present disclosure.

FIG. 3 illustrates a schematic diagram of the operational concept of a transcutaneous hearing device according to an embodiment of the present disclosure.

As illustrated in FIG. 3, in the thus illustrated example implementation, an AM (Amplitude Modulation) modulation signal representing an electromagnetic wave, which carries energy and signal, is received via a wireless link at/by the receiver element of the implantable/implanted unit, wherein the carrier frequency is, e.g. 120 kHz, and the carrier is amplitude modulated with audio frequencies within a range of 100 Hz to 10 kHz. The carrier frequency may be anything from 50 kHz to 10 KHz. By the rectifier element of the implantable/implanted unit, the AM modulation signal is transformed into an upper half waveform (as indicated in the upper dashed-line rounded-corner box) and a lower half waveform (as indicated in the lower dashed-line rounded-corner box). As indicated by bold arrows, the upper half waveform from the AM modulation signal is transferred and thus applied to the one of the vibrators, e.g. VIB1, and the lower half waveform from the AM modulation signal is transferred and thus applied to the other of the vibrators, e.g. VIB2.

As evident from the illustration, in the thus illustrated example implementation, the first vibrator VIB1 is configured to be driven by the upper half waveform of the electromagnetic wave, and the second vibrator VIB2 is configured to be driven by the lower half waveform of the electromagnetic wave. Thereby, the vibrators VIB1 and VIB2 are configured to electromechanically produce vibration using both half waveforms of the AM modulation signal.

In the following, an explanation of the technical effect according to the present disclosure is given.

Conventional transcutaneous hearing devices are known, which use an amplitude-modulated wireless link with a single diode to decode the signal and transfer the signal and energy to a single vibrator. Accordingly, the diode passes only one half of the waveform to drive the vibrator.

As described above, transcutaneous hearing devices according to embodiments of the present disclosure use an amplitude-modulated wireless link with anti-parallel diodes to decode the signal and transfer the signal and energy to two vibrators. Accordingly, the diodes pass both halves of the waveform to drive both vibrators. By utilizing at (at least one) additional diode for passing and an (at least one) additional vibrator for employing the other side of the waveform, two (or more) vibrators can be powered by the same link (i.e. the same transmitted/received energy), and more energy can be utilized.

Thereby, loss of energy over the wireless link of a transcutaneous (bone-conductive) hearing device, i.e. loss of driving energy for the vibrator element, can be compensated or reduced. That is, the vibrator element can be driven with increased energy, as compared with a conventional transcutaneous (bone-conductive) hearing device.

By virtue of embodiments of the present disclosure, the above-explained 10 dB loss of energy in the link can be regained so that the present dual-vibrator transcutaneous active system can have the same or higher sensitivity (maximum force output) as a single-vibrator percutaneous active system.

Figure 4:
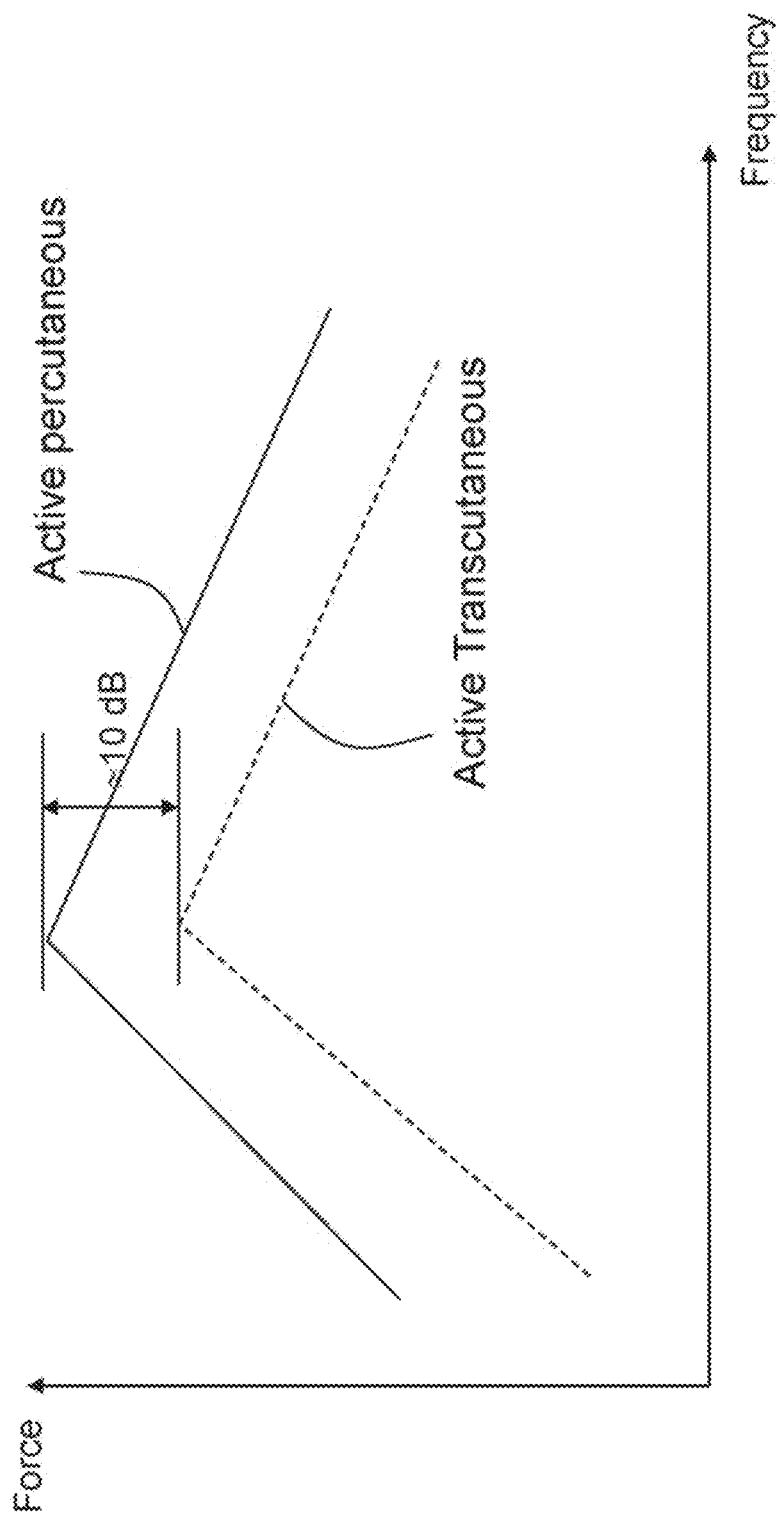
FIG. 4 illustrates a graph depicting the force applied by a vibrator element above the frequency for conventional transcutaneous and percutaneous hearing devices.
Figure 5:
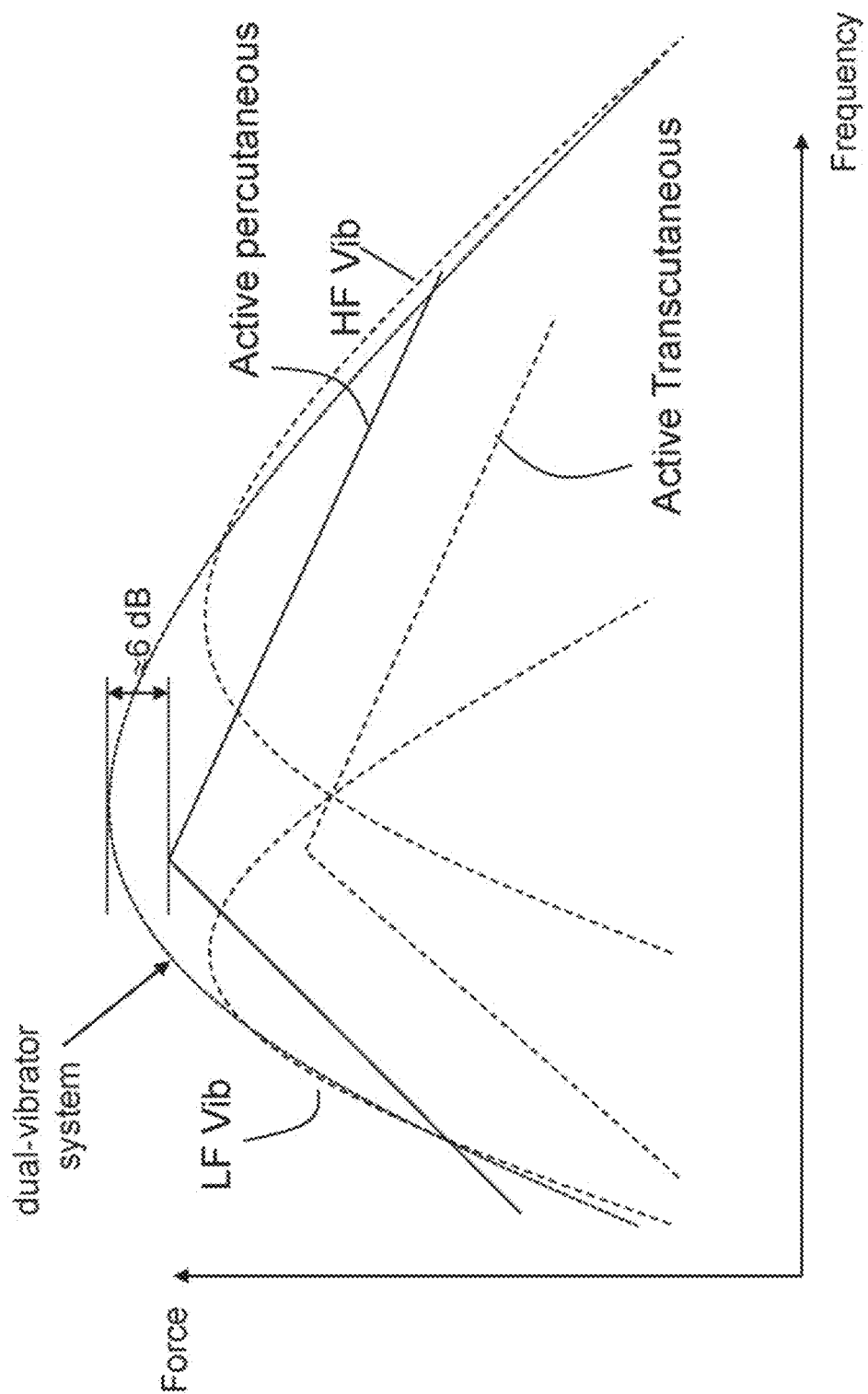
FIG. 5 illustrates a graph depicting the force applied by a vibrator element above the frequency for a transcutaneous hearing device according to an embodiment of the present disclosure, in comparison with conventional transcutaneous and percutaneous hearing devices (as shown in FIG. 4)

This is illustrated in FIGS. 4 and 5 described below.

FIG. 4 illustrates a graph depicting the force applied by a vibrator element above the frequency for conventional transcutaneous and percutaneous hearing devices.

As evident from the frequency characteristics illustrated in FIG. 4, both transcutaneous and percutaneous hearing devices (with a single vibrator) exhibit a single force/sensitivity curve, respectively. At the peak frequency, there is a loss of energy, which is around 10 dB, for a transcutaneous hearing device (with a single vibrator) as compared with a percutaneous hearing device (with a single vibrator), as is explained above.

FIG. 5 illustrates a graph depicting the force applied by a vibrator element above the frequency for a transcutaneous hearing device according to an embodiment of the present disclosure, in comparison with conventional transcutaneous and percutaneous hearing devices (as shown in FIG. 4).

As evident from the frequency characteristics illustrated in FIG. 5, the present transcutaneous hearing device (with two vibrators) exhibits two force/sensitivity curves, one for each of the vibrators. Specifically, there is exemplified a case of usage of a HF vibrator (whose force/sensitivity curve is denoted by "HF Vib") and a LF vibrator (whose force/sensitivity curve is denoted by "LF Vib"). The resulting total force/sensitivity curve of the present dual-vibrator system corresponds to the addition of the two vibrator-related force/sensitivity curves, and is drawn with a dotted line. At the respective peak frequencies, there is a gain of energy, which is around 6 dB, for the present transcutaneous hearing device (with two vibrators) as compared with a conventional percutaneous hearing device (with a single vibrator).

Accordingly, the present dual-vibrator transcutaneous hearing device can outperform even a conventional single-vibrator percutaneous hearing device and, thus, also (and even more) a conventional single-vibrator transcutaneous hearing device.

As is further evident from the frequency characteristics illustrated in FIG. 5, the resulting total force/sensitivity curve of the present dual-vibrator system exhibits a broader shape.

Accordingly, the present dual-vibrator transcutaneous hearing device can provide for a broader force/sensitivity curve, i.e. broadband sensitivity over the frequency can be achieved. The force/sensitivity curve, i.e. the broadband sensitivity, can be adjusted by choosing respective resonance frequencies of the two vibrators, specifically when using a HF vibrator and a LF vibrator.

Figure 6:
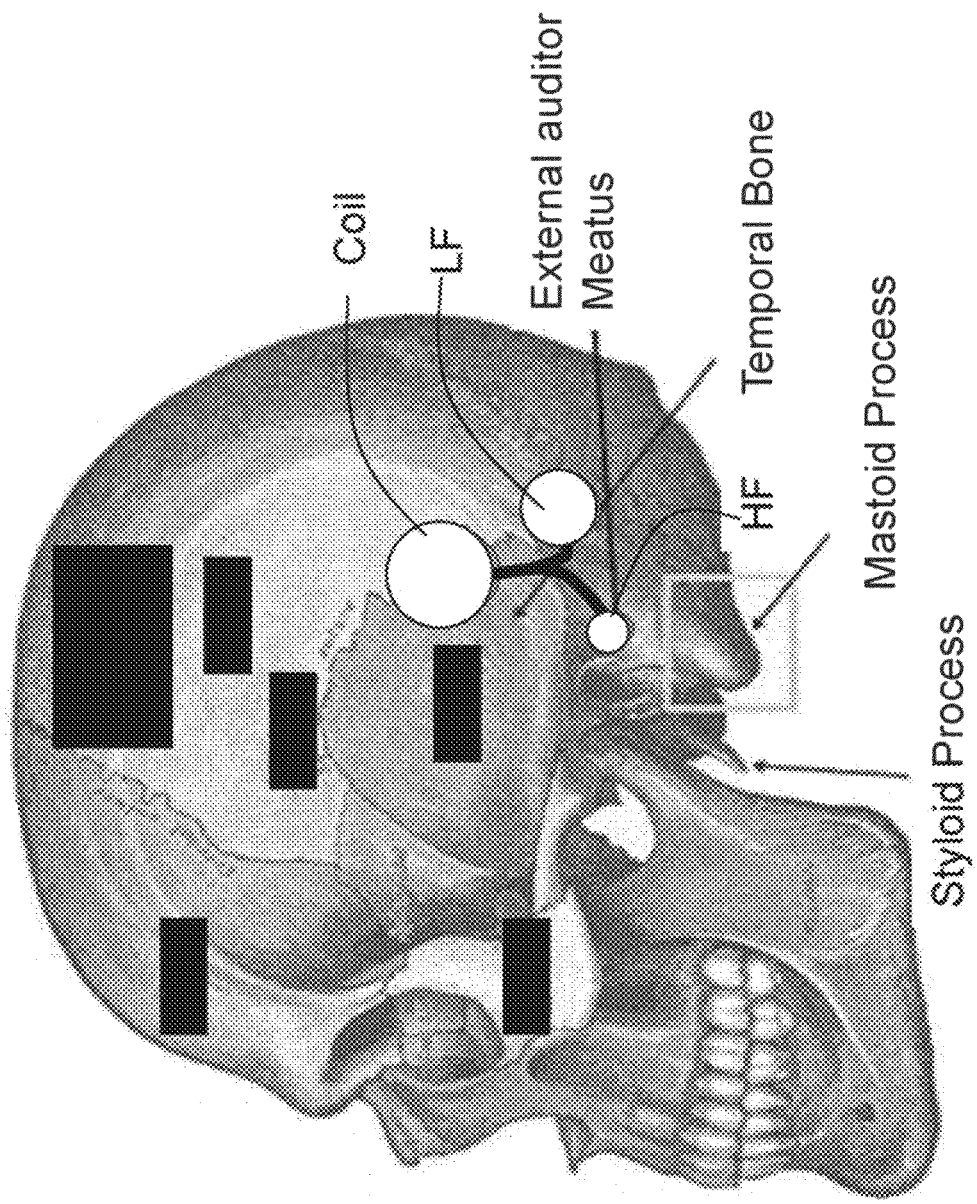
FIG. 6 illustrates examples of placement positions of parts of an implantable unit at a skull according to an embodiment of the present disclosure.

FIG. 6 illustrates examples of placement positions of parts of an implantable unit at a skull according to an embodiment of the present disclosure.

As illustrated in FIG. 6, the receiver element (denoted by "Coil") is configured to be (and is preferably) placed in a border area of the temporal bone and the parietal bone of the skull. Further, the one vibrator, preferably a high-frequency vibrator (denoted by "HF"), is configured to be (and is preferably) placed at the skull to be closer to the cochlea than the other vibrator, preferably a low-frequency vibrator (denoted by "LF"). In such case, the vibrator element may preferably be constituted by two component parts or modules, each of which comprising one of the (HF and LF) vibrators.

In such configuration, adopting the example implementation of the implantable unit as shown in FIG. 2, the receiver element 221 (i.e. the coil I_RX and the capacitor C_RX) may preferably be arranged at the place denoted by "Coil", while the rectifier element 222 and the vibrator element 223 (i.e. the diodes D_VIB1, D_VIB2, the capacitors C_VIB1, C_VIB2 and the vibrators VIB1, VIB2) may preferably be arranged at the places denoted by "HF" and "LF", respectively. Thereby, the receiver and the vibrator are separated as far as possible in order to avoid any interference between the components of the vibrator and the components of the receiver. Furthermore, a configuration with a simple wiring between the receiver and the vibrator can be realized.

Alternatively, the first and second vibrators may also be configured to be (and preferably) placed at basically the same position of the skull. In such case, the vibrator element may preferably be constituted by one component part or module comprising both of the (HF and LF) vibrators.

Typically, it is desirable to place a HF vibrator as close to the cochlea as possible, while a LF vibrator can be placed further back (towards the back of the head). This is because in HF the skull will act as a liquid with wave propagation, while in LF the skull will act more like a rigid mass which makes it not so important to place the vibrator close to the cochlea.

Figure 7:
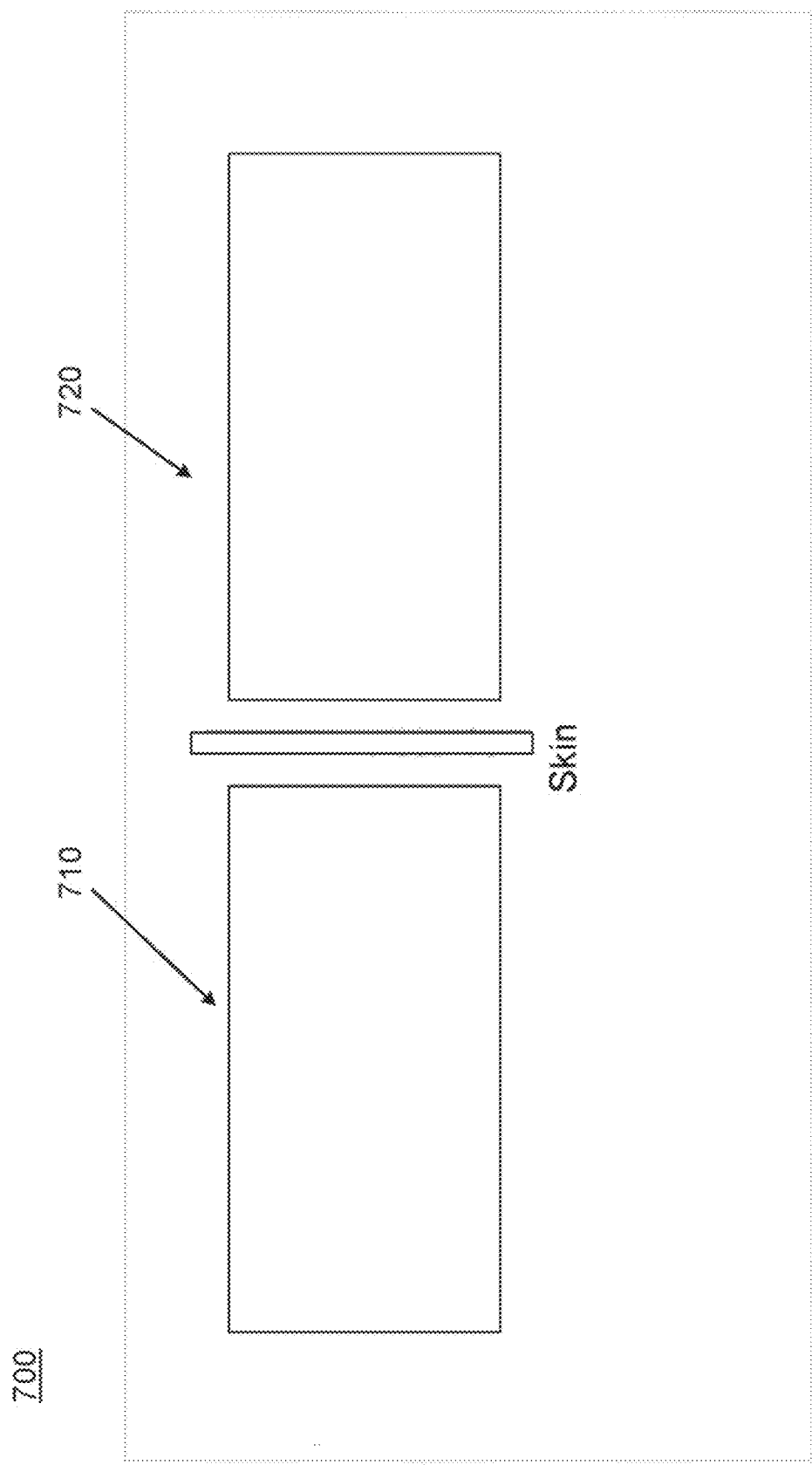
FIG. 7 illustrates a schematic block diagram of an example implementation of a transcutaneous hearing device according to an embodiment of the present disclosure.

FIG. 7 illustrates a schematic block diagram of an example implementation of a transcutaneous hearing device according to an embodiment of the present disclosure. In the thus illustrated example implementation, the implantable unit is operable as a transducer of a Balanced Electromagnetic Separation Transducer (BCI) system.

As illustrated in FIG. 7, a transcutaneous hearing device 700 according to an embodiment comprises an external unit 710 in the form of an external audio processor and an implantable 720 in the form of an implanted unit.

The external audio processor comprises a microphone as an example of a detector element, a DSP (Digital Signal Processor) as an example of a processing element, and an AM (Amplitude Modulator), a tuned driver and a transmitter coil as an example of a transmitter element. In this regard, the AM could also be assigned to the processing element instead of the transmitter element.

The implanted unit comprises a receiver coil as an example of a receiver element, a tuned demodulator as an example of a rectifier element, and a BCI as an example of a vibrator element. According to an embodiment, the tuned demodulator generates upper and lower half waveforms of the electromagnetic wave received via the conductive link, an d the BCI comprises two vibrators which are driven by the upper and lower half waveforms of the electromagnetic wave and thus electromechanically produce vibration using both of the half waveforms of the electromagnetic wave.

In view of the above, it is to be note that embodiments of the present disclosure are described using specific but non-limiting examples. Such examples are used for illustrative purposes, but are by no means intended to limit the technical teaching of the present disclosure. The person skilled in the art will recognize various modifications, alternatives and options which are equally applicable for and/or within the technical teaching of the present disclosure. Such modifications, alternatives and options are readily practicable for the person skilled in the art in view of the present disclosure.

For example, embodiments of the present disclosure are described for a set of one external unit and one implantable unit, i.e. a hearing device/system for one ear. Yet, the technical teaching of the present disclosure is not limited thereto, and a binaural hearing device/system can also be realized thereby. As an example, the above-described set of one external unit and one implantable unit can be provided twice, one for each ear of a user.

For example, embodiments of the present disclosure are described for the example implementation using capacitors and diodes, specifically in the rectifier element and the vibrator element. Yet, the technical teaching of the present disclosure is not limited thereto, and any other implementation of the rectifier element and the vibrator element can be adopted as long as providing the above-described functionalities. Also, any kind and implementation of vibrator can be used, such as a piezo based transducer, as long as the vibrator is able to electromechanically produce vibration (and exert the vibration to the skull of a user of the hearing device when being installed and operative).

For example, embodiments of the present disclosure are described for the example of amplitude modulation, i.e. usage of an amplitude-modulated electromagnetic wave. Yet, the technical teaching of the present disclosure is not limited thereto, and other modulations can equally be used. As an example, frequency modulation or time (variant) modulation can be used for transmission of an electromagnetic wave carrying energy and signal) from an external unit to an implantable (or implanted) unit. Then, the rectifier element and/or the vibrator element are to be configured accordingly in order to enable that (at least) two vibrators can be to driven by the upper and lower half waveforms of the electromagnetic wave in the broadest meaning, namely different (separable) parts of (the energy of) the thus used electromagnetic wave.

For example, embodiments of the present disclosure are described for the example of an electromagnetic (inductive) link between an external unit and an implantable (or implanted) unit, i.e. usage of an analog signal (transmission). Yet, the technical teaching of the present disclosure is not limited thereto, and a digital signal (transmission) can equally be used. Then, the rectifier element and/or the vibrator element are to be configured accordingly. Generally speaking, a fully or at least partly digital implementation of the external unit and/or the implantable unit are conceivable.

In such fully or at least partly digital implementation, at least some functionalities can be realized by computing elements and computer programs.

For example, embodiments of the present disclosure are described for the example of a dual-vibrator realization, i.e. usage of two vibrators in the vibrator element. Yet, the technical teaching of the present disclosure is not limited thereto, and more than two vibrators can equally be used. As an example, three vibrators can be used, wherein one may be a high-frequency (HF) vibrator, one may be a low-frequency (LF) vibrator, and one may be an intermediate-frequency (IF) vibrator. As another example, three or four vibrators can be used, wherein two may be high-frequency (HF) vibrators (potentially having different resonance frequencies) and/or two may be low-frequency (LF) vibrators (potentially having different resonance frequencies).

Generally, the following is also to be noted as regards certain terms as used herein.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include arranging a unit of the hearing device attached to a fixture implanted into the skull bone such as in Bone Anchored Hearing Aid or Cochlear Implant, or arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to provide audible signals to both of the user's ears, whether or not cooperatively. The hearing system or binaural hearing system may further include auxiliary device(s) that communicate(s) with at least one hearing device, any auxiliary device affecting the operation of the hearing devices and/or benefitting from the functioning of the hearing devices. A wired or wireless communication link between the at least one hearing device and the auxiliary device may be established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway may be adapted to receive a multitude of audio signals such as from an entertainment device like a TV or a music player, a telephone apparatus like a mobile telephone or a computer, a PC. The audio gateway may further be adapted to select and/or combine an appropriate one of the received audio signals (or combination of signals)

for transmission to the at least one hearing device. The remote control may be adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device may include i) an input unit such as a microphone for receiving an acoustic signal from a user's surroundings and providing a corresponding input audio signal, and/or ii) a receiving unit for electronically receiving an input audio signal. The hearing device may further include a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously to the skull bone or a vibrator for providing a structure-borne or liquid-borne acoustic signal. In some hearing devices, the output unit may include one or more output electrodes for providing the electric signals such as in a Cochlear Implant.

It is intended that the structural features of the devices described above, either in the detailed description and/or in the claims, may be combined with steps of a corresponding method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

Even though the present disclosure is described above with reference to the examples according to the accompanying drawings, it is to be understood that the present disclosure is not restricted thereto. Rather, it is apparent to those skilled in the art that the present disclosure can be modified in many ways without departing from its scope as disclosed herein.

The claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. Accordingly, the scope should be judged in terms of the claims that follow.

An implantable unit of a transcutaneous hearing device and a transcutaneous hearing device comprising the same are disclosed. The implantable unit comprises a receiver element configured to wirelessly receive an electromagnetic wave, a rectifier element configured to generate upper and lower half waveforms of the electromagnetic wave, and a vibrator element configured to electromechanically or piecoelectric produce vibration using the half waveforms of the electromagnetic wave. The vibrator element comprises a first vibrator and a second vibrator. The first vibrator is configured to be driven by the upper half waveform of the electromagnetic wave, and the second vibrator is configured to be driven by the lower half waveform of the electromagnetic wave.

The invention claimed is:

1. An implantable unit configured to be used in a transcutaneous hearing device, comprising:
   a receiver configured to wirelessly receive an electromagnetic wave,
   a rectifier configured to generate upper and lower half waveforms of the electromagnetic wave, and
   a vibrator configured to electromechanically produce vibration using the half waveforms of the electromagnetic wave,
   wherein the vibrator comprises a first vibrator configured to be driven by the upper half waveform of the electromagnetic wave and a second vibrator configured to be driven by the lower half waveform of the electromagnetic wave,
   the rectifier comprises a first diode in a path from the receiver to the first vibrator and a second diode in a path from the receiver to the second vibrator, and
   the first diode and the second diode are connected with mutually opposite polarity between the receiver and the vibrator.

2. The implantable unit according to claim 1, wherein
   one of the first and second vibrators is a high-frequency vibrator configured to produce high-frequency vibration, and
   the other of the first and second vibrators is a low-frequency vibrator configured to produce low-frequency vibration.

3. The implantable unit according to claim 2, wherein
   the receiver is configured to receive an amplitude-modulated electromagnetic wave, and the rectifier is configured to demodulate the amplitude-modulated electromagnetic wave and to generate upper and lower half waveforms of the amplitude-demodulated electromagnetic wave.

4. The implantable unit according to claim 2, wherein the receiver comprises an configured to inductively receive the electromagnetic wave.

5. The implantable unit according to claim 1, wherein the receiver is configured to receive an amplitude-modulated electromagnetic wave, and
the rectifier is configured to demodulate the amplitude-modulated electromagnetic wave and to generate upper and lower half waveforms of the amplitude- demodulated electromagnetic wave.

6. The implantable unit according to claim 1, wherein the receiver comprises an inductor configured to inductively receive the electromagnetic wave.

7. The implantable unit according to claim 1, wherein the vibrator is constituted by one component part or module comprising the first vibrator and the second vibrator, or
the vibrator is constituted by two component parts or modules, each of which comprising one of the first vibrator and the second vibrator.

8. The implantable unit according to claim 1, wherein the implantable unit is configured to be fixed to a skull of a user of the transcutaneous hearing device.

9. The implantable unit according to claim 8, wherein the receiver is configured to be placed in a border area of a temporal bone and a parietal bone of the skull, and
the first and second vibrators are configured to be placed at a same position of the skull, or one of the first and second vibrators being a high-frequency vibrator is configured to be placed at the skull to be closer to the cochlea than the other of the first and second vibrators being a low-frequency vibrator.

10. The implantable unit according to claim 1, wherein the implantable unit is operable as a transducer of a Bonebridge system, a Bone Conduction Implant system, a Balanced Electromagnetic Separation Transducer system or a variable reluctance type system.

11. A transcutaneous hearing device, comprising:
an implantable unit according to claim 1, and
an external unit configured to operate as an audio processor.

12. The transcutaneous hearing device according to claim 11, wherein the external unit comprises:
a detector configured to detect sound,
a processor configured to generate a sound signal based on the detected sound, and
a transmitter configured to wirelessly transmit the electromagnetic wave based on the sound signal.

* * * * *